(12) United States Patent
Dewey et al.

(10) Patent No.: US 7,862,591 B2
(45) Date of Patent: Jan. 4, 2011

(54) INTERVERTEBRAL PROSTHETIC DEVICE FOR SPINAL STABILIZATION AND METHOD OF IMPLANTING SAME

(75) Inventors: Jonathan Dewey, Memphis, TN (US); Thomas Carls, Memphis, TN (US); Eric C. Lange, Collierville, TN (US); Kent M. Anderson, Memphis, TN (US); Fred J. Molz, IV, Birmingham, AL (US); Matthew M. Morrison, Cordova, TN (US); Aurelien Bruneau, Memphis, TN (US); Jean Taylor, Cannes (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 443 days.

(21) Appl. No.: 11/271,018

(22) Filed: Nov. 10, 2005

(65) Prior Publication Data

US 2007/0123861 A1    May 31, 2007

(51) Int. Cl.
*A61F 2/30* (2006.01)
(52) U.S. Cl. .................. 606/248; 623/17.16; 606/246
(58) Field of Classification Search .................. 606/61, 606/246, 247, 248, 249, 250, 251, 252, 253, 606/254, 255, 256, 257, 258, 259, 260, 261, 606/262, 263, 264, 265, 266, 267, 268, 269, 606/270, 271, 272, 273, 274, 275, 276, 277, 606/278, 279, 280–299, 71–72, 914; 623/17.16, 623/17.11, 17.12–17.15
See application file for complete search history.

(56) References Cited

U.S. PATENT DOCUMENTS

| | | | |
|---|---|---|---|
| 2,677,369 A | 5/1954 | Knowles | |
| 3,648,691 A | 3/1972 | Lumb et al. | |
| 4,011,602 A | 3/1977 | Rybicki et al. | |
| 4,257,409 A | 3/1981 | Bacal et al. | |
| 4,554,914 A | 11/1985 | Kapp et al. | |
| 4,573,454 A | 3/1986 | Hoffman | |
| 4,604,995 A | 8/1986 | Stephens et al. | |
| 4,686,970 A | 8/1987 | Dove et al. | |
| 4,827,918 A | 5/1989 | Olerud | |
| 5,011,484 A | 4/1991 | Breard | |
| 5,047,055 A | 9/1991 | Bao et al. | |
| 5,092,866 A | 3/1992 | Breard et al. | |

(Continued)

FOREIGN PATENT DOCUMENTS

DE    2821678 A1    11/1979

(Continued)

OTHER PUBLICATIONS http://reference.dictionary.com, definition of "bisect" accessed on Aug. 20, 2009.*

(Continued)

*Primary Examiner*—Eduardo C Robert
*Assistant Examiner*—Jan Christopher Merene
(74) *Attorney, Agent, or Firm*—Coats and Bennett, P.L.L.C.

(57) ABSTRACT

An intervertebral prosthetic device and method for spinal stabilization, according to which a prosthetic device is implanted relative to two vertebrae and is positioned so that it makes a rigid connection with one of the vertebra and a non-rigid connection with the other vertebra.

17 Claims, 4 Drawing Sheets

U.S. PATENT DOCUMENTS

| | | | |
|---|---|---|---|
| 5,201,734 A | 4/1993 | Cozad et al. | |
| 5,306,275 A | 4/1994 | Bryan | |
| 5,306,308 A | 4/1994 | Gross et al. | |
| 5,360,430 A | 11/1994 | Lin | |
| 5,366,455 A | 11/1994 | Dove | |
| 5,415,661 A | 5/1995 | Holmes | |
| 5,437,672 A | 8/1995 | Alleyne | |
| 5,454,812 A | 10/1995 | Lin | |
| 5,496,318 A | 3/1996 | Howland et al. | |
| 5,609,634 A | 3/1997 | Voydeville | |
| 5,628,756 A | 5/1997 | Barker, Jr. et al. | |
| 5,634,926 A * | 6/1997 | Jobe | 606/281 |
| 5,645,599 A | 7/1997 | Samani | |
| 5,674,295 A | 10/1997 | Ray et al. | |
| 5,676,702 A | 10/1997 | Ratron | |
| 5,690,649 A | 11/1997 | Li | |
| 5,702,452 A | 12/1997 | Argenson et al. | |
| 5,755,798 A | 5/1998 | Papavero et al. | |
| 5,800,547 A | 9/1998 | Schäfer et al. | |
| 5,810,815 A | 9/1998 | Morales | |
| 5,836,948 A | 11/1998 | Zucherman et al. | |
| 5,860,977 A | 1/1999 | Zucherman et al. | |
| 5,976,186 A | 11/1999 | Bao et al. | |
| 6,022,376 A | 2/2000 | Assell et al. | |
| 6,048,342 A | 4/2000 | Zucherman et al. | |
| 6,059,829 A | 5/2000 | Schläpfer et al. | |
| 6,068,630 A | 5/2000 | Zucherman et al. | |
| 6,113,638 A | 9/2000 | Williams et al. | |
| 6,132,464 A | 10/2000 | Martin | |
| 6,143,031 A | 11/2000 | Knothe et al. | |
| 6,143,032 A | 11/2000 | Schafer et al. | |
| 6,143,033 A | 11/2000 | Paul et al. | |
| 6,179,873 B1 | 1/2001 | Zientek | |
| 6,224,631 B1 | 5/2001 | Kohrs | |
| 6,277,149 B1 | 8/2001 | Boyle et al. | |
| 6,293,949 B1 | 9/2001 | Justis et al. | |
| 6,325,827 B1 | 12/2001 | Lin | |
| 6,352,537 B1 | 3/2002 | Strnad | |
| 6,364,883 B1 | 4/2002 | Santilli | |
| 6,383,221 B1 | 5/2002 | Scarborough et al. | |
| 6,402,750 B1 | 6/2002 | Atkinson et al. | |
| 6,419,703 B1 * | 7/2002 | Fallin et al. | 623/17.11 |
| 6,440,169 B1 | 8/2002 | Elberg et al. | |
| 6,451,019 B1 | 9/2002 | Zucherman et al. | |
| 6,500,178 B2 | 12/2002 | Zucherman et al. | |
| 6,503,279 B1 | 1/2003 | Webb et al. | |
| 6,514,256 B2 | 2/2003 | Zucherman et al. | |
| 6,530,955 B2 | 3/2003 | Boyle et al. | |
| 6,547,823 B2 | 4/2003 | Scarborough et al. | |
| 6,582,433 B2 | 6/2003 | Yun | |
| 6,610,091 B1 * | 8/2003 | Reiley | 623/17.11 |
| 6,613,090 B2 | 9/2003 | Fuss et al. | |
| 6,626,944 B1 * | 9/2003 | Taylor | 623/17.16 |
| 6,645,207 B2 | 11/2003 | Dixon et al. | |
| 6,645,208 B2 * | 11/2003 | Apfelbaum et al. | 606/61 |
| 6,663,632 B1 * | 12/2003 | Frigg | 606/246 |
| 6,695,842 B2 | 2/2004 | Zucherman et al. | |
| 6,706,067 B2 | 3/2004 | Shimp et al. | |
| 6,709,435 B2 | 3/2004 | Lin | |
| 6,723,126 B1 | 4/2004 | Berry | |
| 6,733,534 B2 | 5/2004 | Sherman | |
| 6,761,720 B1 | 7/2004 | Senegas | |
| 6,835,205 B2 | 12/2004 | Atkinson et al. | |
| 6,843,805 B2 | 1/2005 | Webb et al. | |
| 6,946,000 B2 | 9/2005 | Senegas et al. | |
| 6,974,478 B2 * | 12/2005 | Reiley et al. | 623/17.11 |
| 7,041,136 B2 | 5/2006 | Goble et al. | |
| 7,048,736 B2 | 5/2006 | Robinson et al. | |
| 7,087,083 B2 | 8/2006 | Pasquet et al. | |
| 7,101,375 B2 | 9/2006 | Zucherman et al. | |
| 7,163,558 B2 | 1/2007 | Senegas et al. | |
| 7,186,254 B2 * | 3/2007 | Dinh et al. | 606/61 |
| 7,201,751 B2 | 4/2007 | Zucherman et al. | |
| 7,238,204 B2 | 7/2007 | Le Couedic et al. | |
| 7,306,628 B2 | 12/2007 | Zucherman et al. | |
| 7,335,203 B2 | 2/2008 | Winslow et al. | |
| 7,377,942 B2 | 5/2008 | Berry | |
| 7,442,208 B2 | 10/2008 | Mathieu et al. | |
| 7,445,637 B2 | 11/2008 | Taylor | |
| 2001/0012938 A1 * | 8/2001 | Zucherman et al. | 606/61 |
| 2001/0016743 A1 | 8/2001 | Zucherman et al. | |
| 2002/0128654 A1 * | 9/2002 | Steger et al. | 606/69 |
| 2002/0143331 A1 | 10/2002 | Zucherman et al. | |
| 2003/0028250 A1 * | 2/2003 | Reiley et al. | 623/17.11 |
| 2003/0045940 A1 | 3/2003 | Eberlein et al. | |
| 2003/0065330 A1 | 4/2003 | Zucherman et al. | |
| 2003/0153915 A1 | 8/2003 | Nekozuka et al. | |
| 2004/0097931 A1 | 5/2004 | Mitchell | |
| 2004/0199255 A1 | 10/2004 | Mathieu et al. | |
| 2005/0010293 A1 | 1/2005 | Zucherman et al. | |
| 2005/0049708 A1 | 3/2005 | Atkinson et al. | |
| 2005/0149021 A1 * | 7/2005 | Tozzi | 606/61 |
| 2005/0165398 A1 | 7/2005 | Reiley | |
| 2005/0203512 A1 | 9/2005 | Hawkins et al. | |
| 2005/0203624 A1 * | 9/2005 | Serhan et al. | 623/17.11 |
| 2005/0228391 A1 | 10/2005 | Levy et al. | |
| 2005/0261768 A1 | 11/2005 | Trieu | |
| 2005/0288672 A1 | 12/2005 | Feree | |
| 2006/0004447 A1 | 1/2006 | Mastrorio et al. | |
| 2006/0015181 A1 | 1/2006 | Elberg | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0122620 A1 | 6/2006 | Kim | |
| 2006/0129239 A1 | 6/2006 | Kwak | |
| 2006/0136060 A1 | 6/2006 | Taylor | |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0224159 A1 * | 10/2006 | Anderson | 606/61 |
| 2006/0235387 A1 | 10/2006 | Peterman | |
| 2006/0235532 A1 | 10/2006 | Meunier et al. | |
| 2006/0241613 A1 | 10/2006 | Bruneau et al. | |
| 2006/0241757 A1 * | 10/2006 | Anderson | 623/17.11 |
| 2006/0247623 A1 | 11/2006 | Anderson et al. | |
| 2006/0247640 A1 | 11/2006 | Blackwell et al. | |
| 2006/0264938 A1 | 11/2006 | Zucherman et al. | |
| 2006/0271044 A1 | 11/2006 | Petrini et al. | |
| 2006/0271049 A1 | 11/2006 | Zucherman et al. | |
| 2006/0293662 A1 | 12/2006 | Boyer, II et al. | |
| 2006/0293663 A1 | 12/2006 | Walkenhorst et al. | |
| 2007/0005064 A1 * | 1/2007 | Anderson et al. | 606/61 |
| 2007/0043362 A1 | 2/2007 | Malandain et al. | |
| 2007/0100340 A1 * | 5/2007 | Lange et al. | 606/61 |
| 2007/0123861 A1 | 5/2007 | Dewey et al. | |
| 2007/0162000 A1 | 7/2007 | Perkins | |
| 2007/0167945 A1 | 7/2007 | Lange et al. | |
| 2007/0173822 A1 | 7/2007 | Bruneau et al. | |
| 2007/0173823 A1 | 7/2007 | Dewey et al. | |
| 2007/0191833 A1 | 8/2007 | Bruneau et al. | |
| 2007/0191834 A1 | 8/2007 | Bruneau et al. | |
| 2007/0191837 A1 | 8/2007 | Trieu | |
| 2007/0198091 A1 | 8/2007 | Boyer et al. | |

| | | | |
|---|---|---|---|
| 2007/0233068 A1 | 10/2007 | Bruneau et al. | |
| 2007/0233074 A1 | 10/2007 | Anderson et al. | |
| 2007/0233076 A1 | 10/2007 | Trieu | |
| 2007/0233081 A1 | 10/2007 | Pasquet et al. | |
| 2007/0233089 A1 | 10/2007 | DiPoto et al. | |
| 2007/0250060 A1 | 10/2007 | Anderson et al. | |
| 2007/0270823 A1 | 11/2007 | Trieu et al. | |
| 2007/0270824 A1 | 11/2007 | Lim et al. | |
| 2007/0270825 A1 | 11/2007 | Carls et al. | |
| 2007/0270826 A1 | 11/2007 | Trieu et al. | |
| 2007/0270827 A1 | 11/2007 | Lim et al. | |
| 2007/0270828 A1 | 11/2007 | Bruneau et al. | |
| 2007/0270829 A1 | 11/2007 | Carls et al. | |
| 2007/0270834 A1 | 11/2007 | Bruneau et al. | |
| 2007/0270874 A1 | 11/2007 | Anderson | |
| 2007/0272259 A1 | 11/2007 | Allard et al. | |
| 2007/0276368 A1 | 11/2007 | Trieu et al. | |
| 2007/0276496 A1 | 11/2007 | Lange et al. | |
| 2007/0276497 A1 | 11/2007 | Anderson | |
| 2008/0015577 A1* | 1/2008 | Loeb | 606/61 |
| 2008/0021460 A1 | 1/2008 | Bruneau et al. | |
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0215097 A1* | 9/2008 | Ensign et al. | 606/282 |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0105773 A1 | 4/2009 | Lange et al. | |
| 2010/0121379 A1 | 5/2010 | Edmond | |

FOREIGN PATENT DOCUMENTS

| | | |
|---|---|---|
| EP | 0322334 B1 | 2/1992 |
| EP | 1138268 | 10/2001 |
| EP | 1138268 A1 | 10/2001 |
| EP | 1330987 A1 | 7/2003 |
| EP | 1854433 A1 | 11/2007 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799948 A1 | 4/2001 |
| FR | 2816197 A1 | 5/2002 |
| FR | 2858929 | 2/2005 |
| JP | 02-224660 | 9/1990 |
| JP | 09-075381 | 3/1997 |
| SU | 988281 | 1/1983 |
| SU | 1484348 | 7/1989 |
| WO | WO 94/26192 | 11/1994 |
| WO | WO 94/26195 | 11/1994 |
| WO | WO 98/20939 | 5/1998 |
| WO | 02/051326 | 7/2002 |
| WO | WO 2004/047691 A1 | 6/2004 |
| WO | 2005/009300 | 2/2005 |
| WO | WO 2005/009300 A1 | 2/2005 |
| WO | WO 2005/044118 A1 | 5/2005 |
| WO | WO 2005/110258 A1 | 11/2005 |
| WO | WO 2006/064356 A1 | 6/2006 |
| WO | WO 2007/034516 A1 | 3/2007 |
| WO | WO2007052975 A | 5/2007 |

OTHER PUBLICATIONS http://www.thefreedictionary.com, definition for "bisect," accessed on May 18, 2010.*
U.S. Appl. No. 11/261,386, filed Oct. 27, 2005, Lange, et al.
U.S. Appl. No. 11/167,775, filed Jun. 27, 2005, Anderson, et al.
U.S. Appl. No. 11/095,215, filed Mar. 31, 2005, Anderson.
U.S. Appl. No. 11/095,214, filed Mar. 31, 2005, Anderson.
European Patent Office, International Searching Authority, Notification of Transmittal of the International Search Report and the Written Opinion of the International Searching Authority or the Declaration, International Application No. PCT/US2007/062405, Aug. 2, 2007, 9 pages.
"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, ppp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," Spine, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," Spine, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," Spine, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," Spine, 1991, pp. S298-S301, vol. 16, No. 6, Supplement.

* cited by examiner

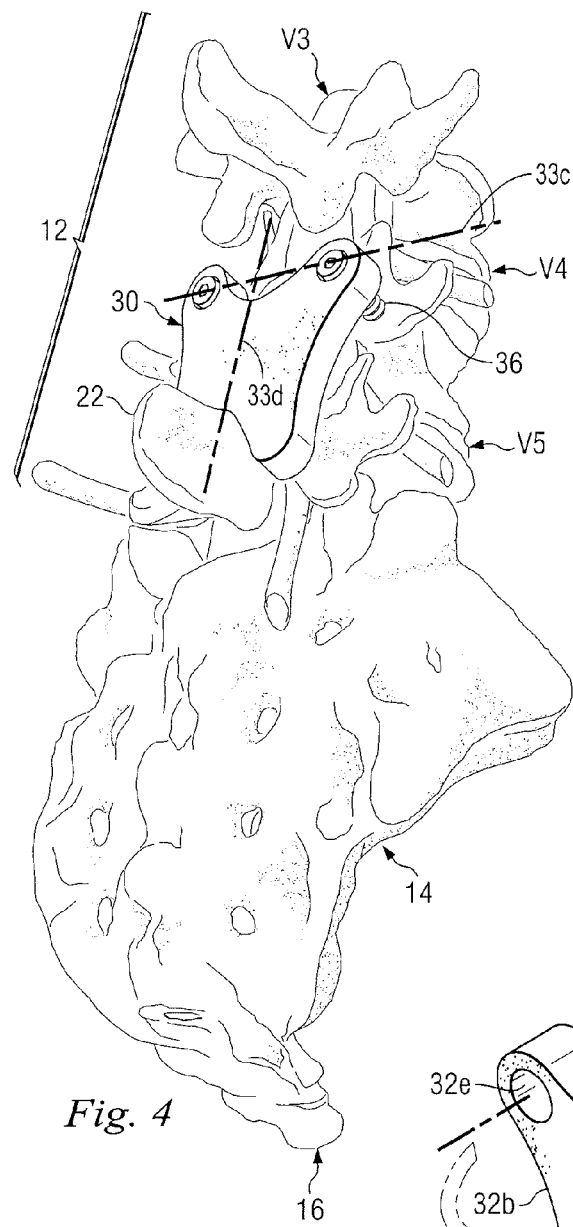
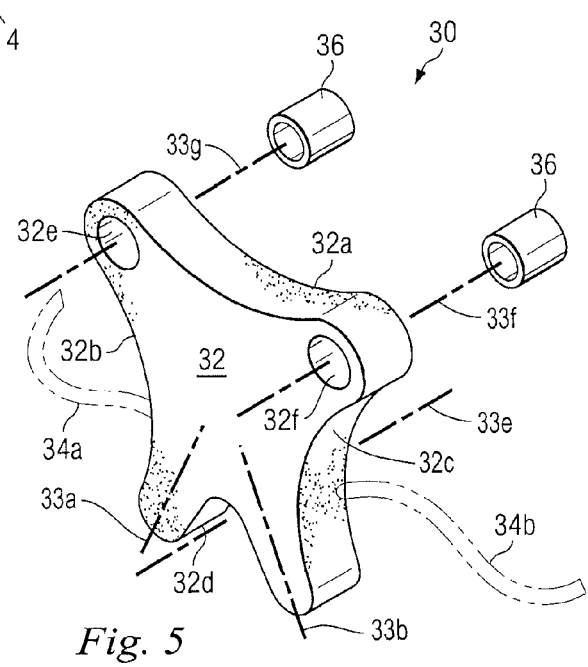
Fig. 4
Fig. 5

INTERVERTEBRAL PROSTHETIC DEVICE FOR SPINAL STABILIZATION AND METHOD OF IMPLANTING SAME

BACKGROUND

The present invention relates to an intervertebral prosthetic device for stabilizing the human spine, and a method of implanting same.

Spinal discs that extend between adjacent vertebrae in vertebral columns of the human body provide critical support between the adjacent vertebrae. These discs can rupture, degenerate, and/or protrude by injury, degradation, disease, or the like to such a degree that the intervertebral space between adjacent vertebrae collapses as the disc loses at least a part of its support function, which can cause impingement of the nerve roots and severe pain.

In these cases, intervertebral prosthetic devices have been designed that can be implanted between the adjacent vertebrae, both anterior and posterior of the column and are supported by the respective spinous processes of the vertebrae to prevent the collapse of the intervertebral space between the adjacent vertebrae and provide motion stabilization of the spine. Many of these devices are supported between the spinous processes of the adjacent vertebrae.

In some situations it is often necessary to perform a laminectomy to remove the laninae and the spinous process from at least one vertebra to remove a intervertebral disc and/or to decompress a nerve root. Typically, in these procedures, two vertebral segments are fused together to stop any motion between the segments and thus relieve the pain. However, since the spinous process is removed from one of the vertebra, it would be impossible to implant a intervertebral prosthetic device of the above type since the device requires support from both spinous processes of adjacent vertebrae.

SUMMARY

According to an embodiment of the invention an intervertebral prosthetic device is provided that is implantable between two adjacent vertebrae, at least one of which is void of a spinous process, to provide motion stabilization.

Various embodiments of the invention may possess one or more of the above features and advantages, or provide one or more solutions to the above problems existing in the prior art.

BRIEF DESCRIPTION OF THE DRAWINGS

FIG. 4 is an isometric view of a portion of the column of FIGS. 1 and 2, depicting an intervertebral prosthetic device according to an embodiment of the invention inserted between two adjacent vertebrae.

FIG. 5 is an enlarged, isometric view of the prosthetic device of FIG. 4.

DETAILED DESCRIPTION

Figure 1:
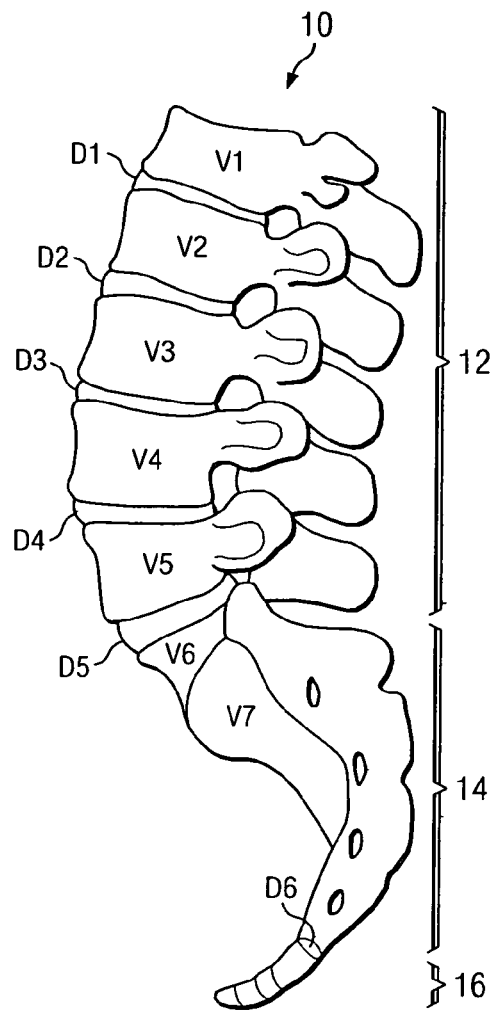
FIG. 1 is a side elevational view of an adult human vertebral column.
Figure 2:
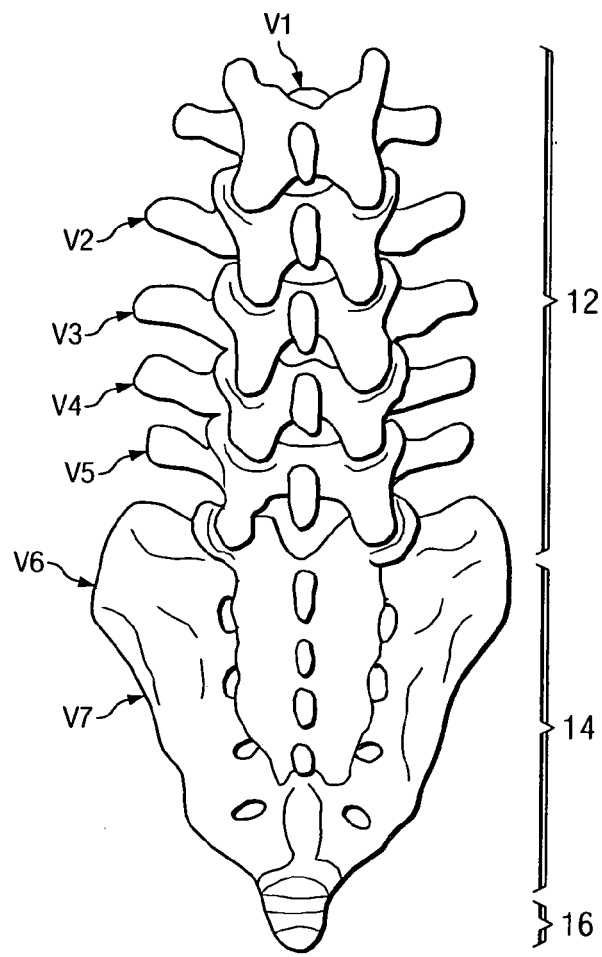
FIG. 2 is a posterior elevational view of the column of FIG. 1.

With reference to FIGS. 1 and 2, the reference numeral 10 refers, in general, to a human vertebral column 10. The lower portion of the vertebral column 10 is shown and includes the lumbar region 12, the sacrum 14, and the coccyx 16. The flexible, soft portion of the vertebral column 10, which includes the thoracic region and the cervical region, is not shown.

The lumbar region 12 of the vertebral column 10 includes five vertebrae V1, V2, V3, V4 and V5 separated by intervertebral discs D1, D2, D3, and D4, with the disc D1 extending between the vertebrae V1 and V2, the disc D2 extending between the vertebrae V2 and V3, the disc D3 extending between the vertebrae V3 and V4, and the disc D4 extending between the vertebrae V4 and V5.

The sacrum 14 includes five fused vertebrae, one of which is a superior vertebra V6 separated from the vertebra V5 by a disc D5. The other four fused vertebrae of the sacurm 14 are referred to collectively as V7. A disc D6 separates the sacrum 14 from the coccyx 16 which includes four fused vertebrae (not referenced).

Figure 3:
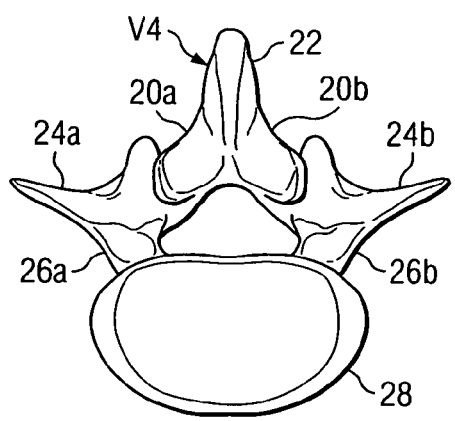
FIG. 3 is an enlarged, front elevational view of one of the vertebra of the column of FIGS. 1 and 2.

With reference to FIG. 3, the vertebra V5 includes two laminae 20a and 20b extending to either side (as viewed in FIG. 2) of a spinous process 22 that projects posteriorly from the juncture of the two laminae. Two transverse processes 24a and 24b extend laterally from the laminae 20a and 20b, respectively, and two pedicles 26a and 26b extend inferiorly from the processes 24a and 24b to a vertebral body 28. Since the other vertebrae V1-V3 are similar to the vertebra V5 they will not be described in detail.

As better shown in FIG. 4, the vertebra V4 is similar to the vertebra V5 with the exception that a laminectomy has been performed to remove the laminae 20a and 20b as well as the spinous process 22 from the vertebra V4 for the reasons set forth above.

An intervertebral disc prosthetic device 30 according to an embodiment of the invention is provided for implanted relative to the vertebrae V4 and V5. The device 30 is shown in detail in FIG. 5 and includes a body member 32 which is substantially rectangular in shape with the exception that the upper end 32a of the body member, as viewed in FIG. 5, as well as the two sides 32b and 32c, are curved inwardly to form concave surfaces. A curved saddle, or notch, 32d is formed in the other end portion of the body member 32. The notch 32d forms a concave surface having two opposing lobes, each having a centerline 33a, 33b that extends along the length of the lobe. The centerlines 33a, 33b of the lobes extend in diverging directions. Two through openings 32e and 32f are formed through the body member 32 at the upper corners thereof. Two sleeves 36 are adapted to fit into the openings 32e and 32f, respectively, to strengthen the opening, and two tethers 34a and 34b can be connected at one end to the body member 32 and can be tied to the vertebrae V4 and/or V5 in a conventional manner. Since the tethers 36a and 36b are optional, they are shown in phantom lines. As shown in FIGS. 4-5, a first theoretical axis 33c extends through the centers of the openings 32e and 32f. A second theoretical axis 33d extends substantially normal to the first axis 33c and bisects a distance between the pair of openings 32e, 32f and extends through the notch 32d. In addition, a third theoretical axis 33e extends from the posterior surface to the anterior surface of the body member 32, while the pair of openings 32e and 32f extend along fourth and fifth theoretical axes 33f and 33g respectively. The third theoretical axis 33*e* extends approximately parallel to the fourth and fifth theoretical axes 33*f* and 33*g*.

Figure 6:
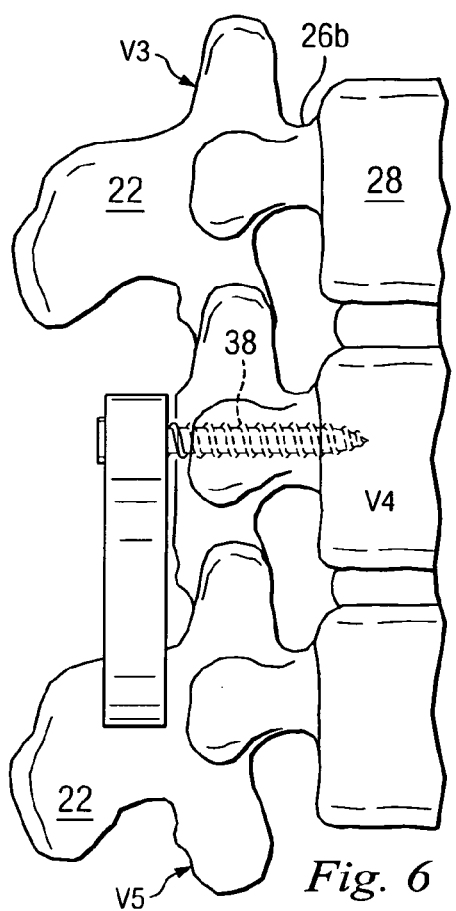
FIG. 6 is an enlarged, sectional view depicting the implanted prosthetic device of FIGS. 4 and 5.

When the device 30 is implanted relative to the vertebrae V4 and V5 as shown in FIGS. 4 and 6, the device is positioned so that the spinous process 22 of the vertebra V5 extends in the notch 32*d*. The body member 32 is sized so that, in this position, the openings 32*e* and 32*f* extend over the pedicles 26*a* and 26*b* of the vertebra V4. Then, two screws 38, one of which is shown in FIG. 6, are inserted through the sleeves 36 in the openings 32*e* and 32*f*, respectively (FIG. 5), of the body member 32 and torque is applied to the screws so that they are driven into the respective pedicles 26*a* and 26*b* of the vertebrae V4 and V5 to provide compressional and torsional resistance. The screws 38 can be of any conventional type and therefore will not be described in detail.

Thus, the device 30 is connected to the vertebra V5 by a non-rigid connection provided by the notch 32*d*, and to the vertebra V4 by a rigid connection provided by the screws 38, notwithstanding the fact that the spinous process of the vertebra V4 is missing. The tethers 34*a* and 34*b* can also be tied to the vertebrae V4 and/or V5 to provide additional distracting resistance.

The materials making up the body member 32 can vary within the scope of the invention. For example the body member 32 can be fabricated from a relatively soft material and/or a relatively hard material, or both. In the last case, a relatively soft outer layer, such as silicone, could be molded around a relatively stiff inner layer, such as hard rubber or plastic.

Figure 7:
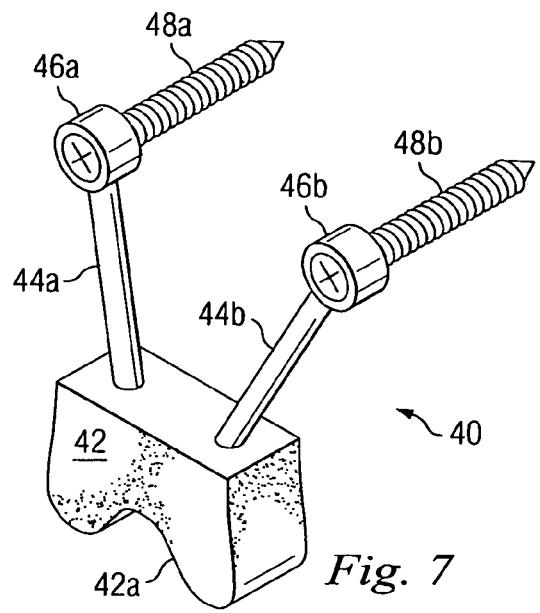
FIG. 7 is a view similar to that of FIG. 5, but depicting an alternate embodiment of the invention.

A prosthetic device according to an alternate embodiment is shown, in general, by the reference numeral 40 in FIG. 7. The device 40 includes a body member 42 having a saddle, or curved notch 42*a* formed in one end thereof which is the lower end as viewed in FIG. 7. Two arms 44*a* and 44*b* extend from the other end of the body member 42 and at an angle to the vertical so that their distal ends extend over the pedicles 26*a* and 26*b* (FIGS. 3 and 4) of the vertebra V4. Two retaining rings 46*a* and 46*b* are mounted to the distal ends of the arms 44*a* and 44*b*, respectively, in any conventional manner, and are adapted to receive two screws 48*a* and 48*b*, respectively. The retaining rings 46*a* and 46*b*, as well as the screws 48*a* and 48 can be of any conventional type and therefore will not be described in detail.

The device 40 is implanted relative to the vertebrae V4 and V5, so that the spinous process 22 of the vertebra V5 extends in the notch 42*a* of the body member 42. The screws 48*a* and 48*b* are inserted through the rings 46*a* and 46*b*, respectively, and torque is applied to the screws so that they are driven into the pedicles 26*a* and 26*b* (FIG. 3) of the vertebra V4 which provides compressional and torsional resistance.

Thus, the device 40 is secured in its implanted position by both a non-rigid connection to the vertebra V5 provided by the notch 42*a*, and a rigid connection to the vertebra V4 provided by the screws 48*a* and 48*b*, notwithstanding the fact that the spinous process from the vertebra V4 is missing.

It is understood that the tethers 36*a* and 36*b* of the embodiment of FIGS. 5 and 6 can also be connected to the body member 42 and tied to the vertebrae V4 and/or V5 to provide additional distracting resistance.

Figure 8:
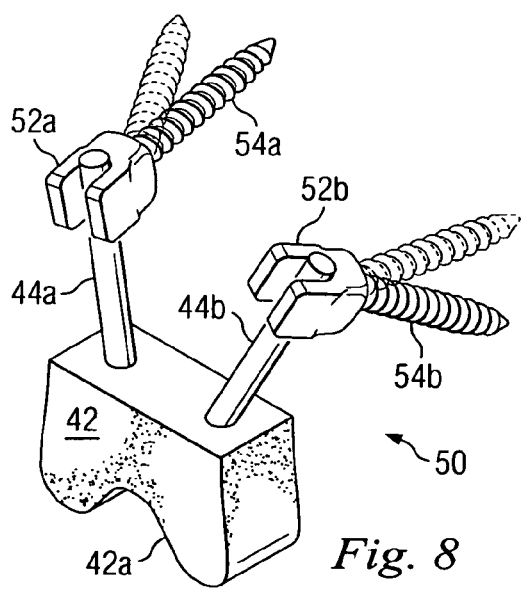
FIG. 8 is a view similar to that of FIG. 7, but depicting an alternate embodiment of the invention using multiaxial screws.

A prosthetic device according to an alternate embodiment is shown, in general, by the reference numeral 50 in FIG. 8, and includes several components of the embodiment of FIG. 7 which components are given the same reference numerals. As in the previous embodiment, it will be assumed that a laminectomy has been performed to remove the laminae 20*a* and 20*b* (FIG. 3) and the spinous process 22 from the vertebra V4 for the reasons set forth above. The device 50 includes the body member 42 of the embodiment of FIG. 7 that has a saddle, or curved notch, 42*a* formed in one end thereof which is the lower end as viewed in FIG. 8. The two arms 44*a* and 44*b* of the embodiment of FIG. 7 are also provided and extend from the other end of the body member 42 and, preferably at an angle to the vertical so that their distal ends extend over the pedicles 26*a* and 26*b* (FIGS. 3 and 4) of the vertebra V4.

Two U-shaped clamps 52*a* and 52*b* are clamped around the distal end portions of the arms 44*a* and 44*b*, respectively. Each clamp 52*a* and 52*b* can be designed so that its two legs have spring tension permitting the distal end portions of the arms 44*a* and 44*b* to be clamped between the legs. It is understood that, if necessary, fasteners, or the like, can be used to secure the connections.

Two multiaxial screws 54*a* and 54*b* are supported in the bases of the clamps 52*a* and 52*b* respectively, in a conventional manner, so that the screws can be pivoted relative to the clamps to change the angular positions of the screws. Examples of two positions that the screws 54*a* and 54*b* can take are shown in FIG. 8 by the solid lines and the phantom lines, respectively, it being understood that the screws can take numerous other positions.

The device 50 is implanted relative to the vertebrae V4 and V5, so that the spinous process 22 of the vertebra V5 extends in the notch 42*a* of the body member 42. The screws 54*a* and 54*b* are placed at the proper angle relative to the pedicles 26*a* and 26*b* (FIG. 3) of the vertebra V4, and torque is applied to the screws so that they are driven into the pedicles to provide compressional and torsional resistance.

Thus, the device 50 is secured in its implanted position by both a non-rigid connection to the vertebra V5 provided by the notch 42*a*, and a rigid connection to the vertebra V4 provided by the screws 54*a* and 54*b*, notwithstanding the fact that the spinous process from the vertebra V4 is missing.

It is understood that the tethers 36*a* and 36*b* of the embodiment of FIGS. 5 and 6 can also be connected to the body member 42 of each of the above embodiment and tied to the vertebrae V4 and/or V5 to provide additional distracting resistance.

Figure 9:
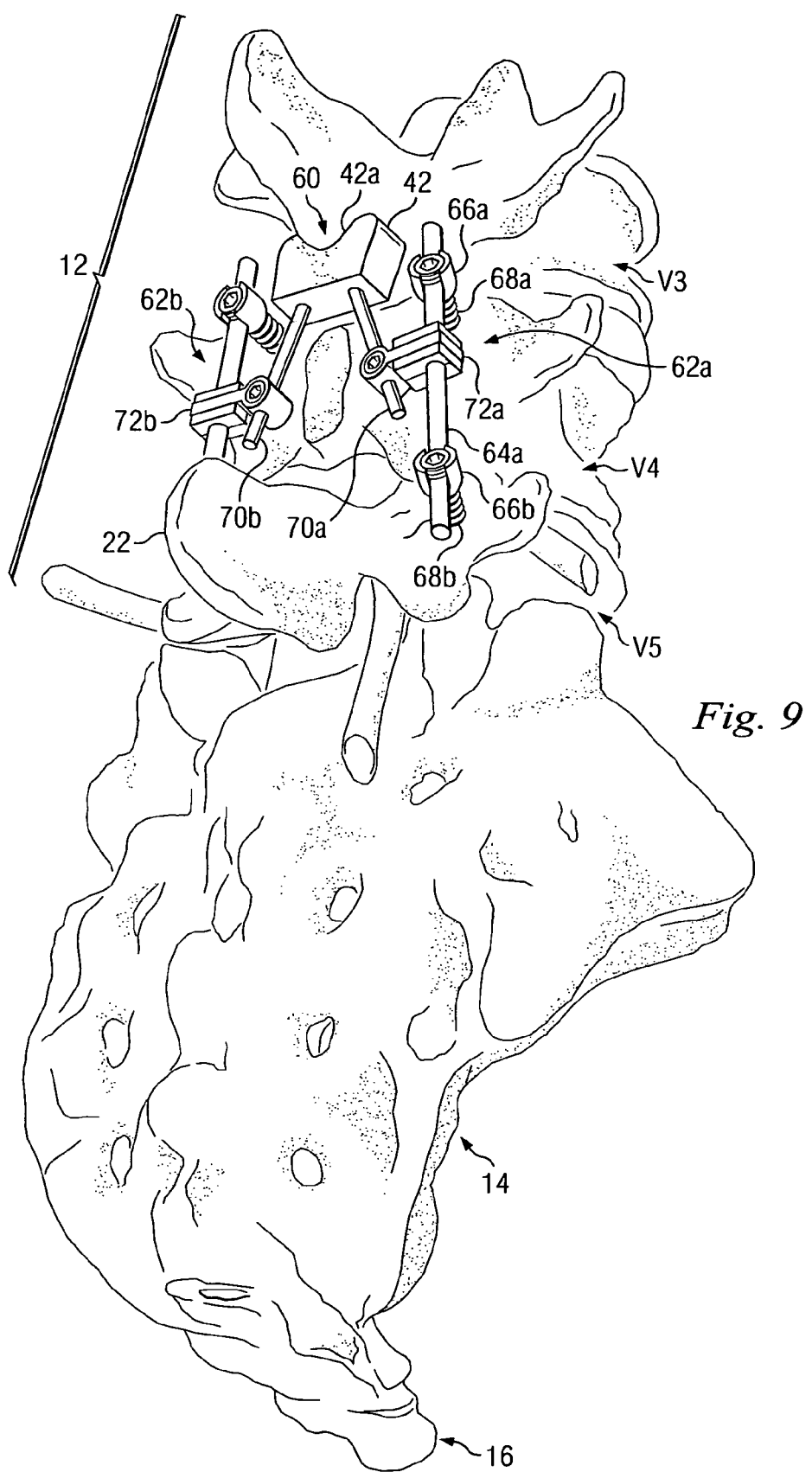
FIG. 9 is a view similar to FIG. 4, but depicting an alternate embodiment of the invention.

A device according to another alternate embodiment is shown, in general by the reference numeral 60 in FIG. 9. In the figure, the spinous process 22 from vertebra V4 has been removed. A complete laminectomy as described in previous embodiments could be performed at the V4 level as well.

The device 60 is designed to be used with two constructs 62*a* and 62*b* that extend between, and to the sides of, the location of the above laminectomy. It is understood that, in most circumstances, the constructs 62*a* and 62*b* would have been implanted in this manner in a previous procedure for the purpose of providing immobilization and/or stabilization to the spinal system, and/or to serve as an adjunct to fusion of one or more portions of the spinal system.

The construct 62*a* consists of a rod 64*a* having a pair of spaced mounting rings 66*a* and 66*b* connected to the rod near its respective ends. The mounting rings 66*a* and 66*b* receive pedicle screws 68*a* and 68*b*, respectively that are threadably engaged with the pedicle 20*b* (FIG. 3) on one side of the vertebra V4 and the corresponding pedicle on the vertebra V5. Since the construct 62*b* is identical to the construct 62*a*, it will not be described in detail, it being understood that its pedicle screws are threadably engaged with the pedicle 20*a* (FIG. 3) on the other side of the vertebra V4 and the corresponding pedicle of the vertebra V5, respectively The device 60 includes the body member 42 of the embodiment of FIG. 7 that has a saddle, or curved notch 42*a* formed in one end thereof which is the upper end as viewed in FIG. 9.

Two arms 70a and 70b extend from the other end of the body member 42 and, preferably at an angle to the vertical, and two U-shaped clamps 72a and 72b are affixed near the distal ends of the arms 70a and 70b, respectively. The clamp 72a is adapted to clamp over the arm 64a of the construct 62a, and the clamp 72b is adapted to clamp over the corresponding arm of the construct 62b. Since the clamps 72a and 72b are conventional, they will not be described in detail.

The device 60 is implanted relative to the vertebrae V3 and V5, so that the spinous process 22 of the vertebra V3 extends in the notch 42a of the body member 42. The arms 70a and 70b are adjusted as necessary so that the clamp 72a extends over the rod 64a of the construct 62a between the mounting rings 66a and 66b; and the clamp 72b extends over the rod of the construct 62b between its respective mounting rings. The clamps 72a and 72b are then clamped to the rod 64a and the rod of the construct 62b to secure the member 42 to the constructs 62a and 62b.

Thus, the device 60 is secured in its implanted position by both a non-rigid connection to the vertebra V3 provided by the notch 42a in the member 42, and a rigid connection to the vertebrae V4 and V54 provided by the above connection of the device 60 to the construct 62.

It is understood that the lengths of the rods 64a and 64b can be greater than that shown and discussed in the example above in which case additional mounting rings, identical to the rings 66a and 66b, would also be connected to the rods. Also, the pedicle screw 66a, and the corresponding screw associated with the construct 62b, can be located so that they extend in the pedicles of the vertebra V3 as described above or in the pedicles of the vertebra V4; while the pedicle screw 66b, and the corresponding screw associated with the construct 62b, can be located so that they extend in the pedicles of the vertebra V4 as described above or in the pedicles of the vertebra V5.

Additionally, it is understood that the arms 70a and 70b could be long enough such that the embodiment could be mounted to a construct 62a or 62b while the member 42 could rest against a non-adjacent spinous process 22. For example, the member 42 could be nested against the spinous process 22 of VI with the construct 62a or 62b anchored between V4 and V5.

In each of the above embodiments, the materials making up the body member 42 can vary within the scope of the invention. For example, the body member 42 can be fabricated from a relatively hard material and/or a relatively soft material, or both. In the last case, a relatively soft outer layer such as silicone, could be molded around a relatively stiff inner layer, such as hard rubber or plastic.

Variations

It is understood that variations may be made in the foregoing without departing from the invention and examples of some variations are as follows:

The above non-rigid connection can be to one of the vertebrae V3, V4 or V5, and the rigid connection to another.

The body member 32 can be provided with additional openings to receive additional screws that could be driven in the vertebrae V4 and/or V5.

The body members 32 and 42 can vary in shape, size, composition, and physical properties.

The surfaces of the body member defining the notch 32d can be treated, such as by providing teeth, ridges, knurling, etc., to better grip the spinous process.

The body members 32 and 42 can be fabricated of a permanently deformable material thus providing a clamping action against the spinous process.

Any conventional substance that promotes bone growth, such as HA coating, BMP, or the like, can be incorporated in the prosthetic device of each of the above embodiments.

The body members 32 and 42 can have through holes formed therein to improve integration of the bone growth.

The devices 30, 40, 50 and 60 can be implanted relative to two vertebrae in the vertebral column 10 other than the vertebrae V4 and V5.

Bilateral extrusions, or the like, can be provided on one or more of the body members 32 and 42 to enable a tether to be attached to the body member.

The prostheses of the above embodiments can be inserted between two vertebrae following a discectomy in which a disc between the adjacent vertebrae is removed, or corpectomy in which at least one vertebra is removed.

The screws 36, 48a, 48b, 54a, 54b, 68a. and 68b can extend into areas of the vertebra V4 other than the pedicles 26a and 26b. For example, the pedicle screw 68a of the construct 62a, and the corresponding screw of the construct 62b, can engage the vertebra V3 rather than the vertebra V4; and the pedicle screw 68b of the construct 62a, and the corresponding screw of the construct 62b can engage the vertebra V4 rather than the vertebra V5.

The spatial references made above, such as "under", "over", "between", "upper", "lower", "top", "bottom", "side", etc. are for the purpose of illustration only and do not limit the specific orientation or location of the structure described above.

The preceding specific embodiments are illustrative of the practice of the invention. It is to be understood, therefore, that other expedients known to those skilled in the art or disclosed herein, may be employed without departing from the invention or the scope of the appended claims, as detailed above. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw are equivalent structures.

What is claimed is:

1. A prosthetic device, comprising:
a monolithic body member comprising:
    a concave upper surface;
    a pair of opposing concave side surfaces;
    a concave lower surface opposite the concave upper surface, the concave lower surface defining a notch sized for non-rigidly receiving a spinous process of a first vertebra; the concave lower surface having two opposing lobes;
    an upper portion of the body member, disposed proximate the concave upper surface and having a pair of through openings extending therethrough, each of the through openings positioned adjacent an upper corner of the body member such that when the spinous process of the first vertebra is received within the notch defined by concave lower surface the pair of through openings are substantially aligned with an adjacent second vertebra such that bone anchors may be inserted through the through openings to rigidly secure the body member to the second vertebra;

a lower portion of the body member, disposed proximate the notch, being devoid of through openings;

wherein a first theoretical axis extends through centers of the pair of through openings;

wherein a second theoretical axis extending substantially normal to the first theoretical axis bisects a distance between the pair of through openings into two equal lengths and extends through the notch;

wherein each of the two opposing lobes includes a centerline that extends in a direction from a base to a tip of the lobe; wherein the base of each lobe is disposed more proximate to the through openings and the tip of each lobe is disposed more distal to the through openings; the centerlines of two opposing lobes extending in diverging directions.

2. The prosthetic device of claim 1, further comprising a pair of sleeves positioned within the through openings.

3. The prosthetic device of claim 1, further comprising a pair of tethers connected to the body member.

4. The prosthetic device of claim 1, wherein the body member has an upper width adjacent the upper surface and a lower width adjacent the lower surface, the upper width being greater than the lower width.

5. The prosthetic device of claim 4, wherein the body member is formed substantially of a relatively soft material.

6. The prosthetic device of claim 4, wherein the body member is formed substantially of a relatively rigid material.

7. The prosthetic device of claim 4, wherein the body member comprises an inner portion formed of a first material and an outer portion formed of a second material, wherein the first material is more rigid than the second material.

8. The prosthetic device of claim 4, wherein the body member comprises a substantially uniform thickness.

9. The prosthetic device of claim 1 wherein the body member further comprises a posterior surface and an anterior surface spaced from each other and disposed generally transverse to the upper surface, the lower surface, and the side surfaces; wherein the notch extends from the posterior surface to the anterior surface.

10. The prosthetic device of claim 9 wherein the pair of through openings extend from the posterior surface to the anterior surface and are oriented generally parallel to the notch.

11. The prosthetic device of claim 9 wherein, when the notch receives the first vertebra:

the notch is configured to intersect a sagittal plane defined by the first and second vertebra; and the pair of through openings are configured to extend substantially parallel to the sagittal plane.

12. The prosthetic device of claim 9 wherein:

the notch extends along a third theoretical axis extending from the posterior surface to the anterior surface of the body member; and the pair of through openings extend along fourth and fifth theoretical axes respectively, the fourth and fifth theoretical axes extending approximately parallel to the third theoretical axis.

13. The prosthetic device of claim 1 wherein:

the body member comprises first and second pairs of outwardly extending lobes;

the pair of through openings associated with the first pair of lobes;

the second pair of lobes disposed proximate the notch.

14. The prosthetic device of claim 13 wherein said second pair of lobes are spaced farther apart than said first pair of lobes.

15. The prosthetic device of claim 9 wherein the body member has a substantially uniform thickness from the posterior surface to the anterior surface from a first of the side surfaces to the other of the side surfaces.

16. A prosthetic device, comprising:

a monolithic body member comprising at least one concave surface defining a notch sized for non-rigidly receiving a spinous process of a first human vertebra;

a pair of through openings extending through the body member; each of the through openings positioned on the body member such that when the spinous process of the first vertebra is received within the notch defined by the concave surface, the pair of through openings are substantially aligned with an adjacent second vertebra such that bone anchors may be inserted through the through openings to rigidly secure the body member to the second vertebra;

wherein the body member comprises first and second pairs of outwardly extending lobes; the first pair of lobes is associated with the through openings and the second pair of lobes is disposed proximate the notch and is devoid of through openings;

wherein a first theoretical axis extends through centers of the pair of through openings;

wherein a second theoretical axis extending substantially normal to the first theoretical axis bisects a distance between the pair of through openings into two equal lengths and extends through the notch;

wherein each lobe of the second pair of lobes includes a centerline that extends in a direction from a base to a tip of the lobe;

wherein the base of each of the second pair of lobes is disposed more proximate to the through openings and the tip of each of the second pair of lobes is disposed more distal to the through openings; the centerlines of the second pair of lobes extending in diverging directions.

17. The prosthetic device of claim 16 wherein said first pair of lobes are spaced farther apart than said second pair of lobes.

* * * * *